(12) United States Patent
Torikai et al.

(10) Patent No.: US 8,716,679 B2
(45) Date of Patent: May 6, 2014

(54) BEAM IRRADIATION APPARATUS AND BEAM IRRADIATION CONTROL METHOD

(75) Inventors: Kota Torikai, Maebashi (JP); Satoru Yamada, Maebashi (JP)

(73) Assignee: National University Corporation Gunma University, Maebashi-shi (JP)

(*) Notice: Subject to any disclaimer, the term of this patent is extended or adjusted under 35 U.S.C. 154(b) by 0 days.

(21) Appl. No.: 13/519,811

(22) PCT Filed: Aug. 5, 2010

(86) PCT No.: PCT/JP2010/063253
§ 371 (c)(1),
(2), (4) Date: Aug. 17, 2012

(87) PCT Pub. No.: WO2011/080942
PCT Pub. Date: Jul. 7, 2011

(65) Prior Publication Data
US 2012/0316378 A1 Dec. 13, 2012

(30) Foreign Application Priority Data
Dec. 28, 2009 (JP) ................................. 2009-298316

(51) Int. Cl.
*G21K 5/04* (2006.01)

(52) U.S. Cl.
USPC ................. 250/492.1; 250/492.3; 250/396 R; 250/396 ML (58) Field of Classification Search
USPC ........ 250/492.1, 492.3, 396 R, 396 ML, 397, 250/398
See application file for complete search history.

(56) References Cited

U.S. PATENT DOCUMENTS

2004/0162457 A1* 8/2004 Maggiore et al. ................. 600/1

FOREIGN PATENT DOCUMENTS

| JP | 10-118204 A | 5/1998 |
| JP | 2001-562 A | 1/2001 |
| JP | 2001-212253 A | 8/2001 |
| JP | 2006-208200 A | 8/2006 |
| JP | 2007-268035 A | 10/2007 |
| JP | 2009-22797 A | 2/2009 |

OTHER PUBLICATIONS

Torikai, Kota, et al., "Carbon-Ion Beam Port Design for Heavy-Ion Microbeam Surgery", Proceedings of Particle Accelerator Society Meeting, Web URL: http://www.pasj.jp/web_publish/pasj6/papers/toapa03.pdf, p. 755-757 (2009), w English abstract.

(Continued)

*Primary Examiner* — Nicole Ippolito
(74) *Attorney, Agent, or Firm* — Westerman, Hattori, Daniels & Adrian, LLP (57) ABSTRACT

The beam irradiation apparatus is featured by including a transport pipe which is vacuum-evacuated to be used as a transport channel of a beam taken out from an accelerator, a quadrupole magnet which modulates the beam diameter of the beam so that the beam is incident on an irradiation target existing in the atmosphere while maintaining the focusing angle of the beam, and one or more longitudinally movable range shifters which are provided to be capable of changing the distance to the irradiation target of the beam, and which modulate the beam range by reducing the energy of the beam by allowing the beam to pass through the movable range shifter, and is featured in that the beam is irradiated onto the irradiation target by modulating the beam diameter and the beam range.

14 Claims, 5 Drawing Sheets

(56) References Cited

OTHER PUBLICATIONS

Minohara, Shinichi, "Cancer Treatment in the 21st Century, Basics and Clinical Treatment of Heavy Particle Radiotherapy" edited by Hirohiko Tsujii, Iryo Kagaku Sha, p. 31-42.

Particle Accelerator Society Meeting (6th), Web URL: http://www.pasj.jp/dai6kainenkai/, Aug. 6, 2009 (8 pages).

Torikai, Kota, et al., "Carbon-Ion Beam Port Design for Heavy-Ion Microbeam Surgery", Proceedings of Particle Accelerator Society Meeting, Web URL: http://www.paskjp/web_publish/pasj6/papers/toapa03.pdf, p. 755-757 (2009), w English abstract.

International Search Report of PCT/JP2010/063253 date of mailing Aug. 31, 2010.

International Preliminary Report on Patentability (Form PCT/IB/373) of International Application No. PCT/JP2010/063253 dated Jun. 28, 2011, w/ English translation, with Form PCT/ISA/237 dated Aug. 31, 2010.

* cited by examiner

BEAM IRRADIATION APPARATUS AND BEAM IRRADIATION CONTROL METHOD

TECHNICAL FIELD

The present invention relates to irradiation control of a beam. More particularly, the present invention relates to a beam irradiation apparatus which is capable of reducing, to a very small value, the diameter of a beam taken out from an accelerator and which is further capable of modulating the beam diameter, the beam range, and the beam trajectory, and also relates to a method for controlling beam irradiation, in which the range of an irradiation field in an irradiation target can be modulated with high accuracy.

BACKGROUND ART

In cancer therapy, heavy particle radiotherapy using heavy ions, such as carbon ions, is featured by high biological effect on tumor, high dose concentration, and low-dose exposure to normal tissue surrounding a lesion. The known heavy particle radiotherapy includes a process of confirming a treatment region on the basis of prior diagnosis using a CT, and the like, a treatment planning process in which the beam diameter, the beam range, and the beam scan width are determined according to the treatment region, and a process of performing the irradiation according to the treatment plan. In a therapy apparatus used for the therapeutic irradiation, a quadrupole magnet is inserted at a beam transport line to modulate the diameter of a beam during beam transportation, and the irradiation position of the beam. Also, a ridge filter and a range shifter are provided, which enable the irradiation thickness and the irradiation position of the beam in an irradiation target to be changed. Optimum irradiation conditions about the beam diameter, the beam range, the beam scan width, and the like, are determined by performing beam simulation. In order to realize a beam transport system of heavy particles, a beam transport optical system, which is configured by a transport pipe evacuated to high vacuum, and various electromagnets which modulate the formation of the beam shape and the beam trajectory, needs to be designed so as to satisfy the beam specification required for using the beam. Further, in view of both machining accuracy and cost, it is desired that the weight of components configuring the beam transport system is small. For this reason, the inner diameter of the transport pipe is set to about several tens mm in order to reduce the weight of various electromagnets (Cancer Treatment in the 21st Century, Basics and Clinical Treatment of Heavy Particle Radiotherapy, edited by Hirohiko Tsujii, and published by Iryo Kagaku Sha, ISBN4-900770-83-3 C3047).

On the other hand, in cancer treatment, the diameter of the irradiation field needs to be set to about 210 mm in order to cope with the irradiation to the whole pelvic area, and the like. In order to satisfy this requirement, a conventional method for controlling beam irradiation (wobbler irradiation method) is described in Patent Literature 1 (1).

In the wobbler irradiation method, in order to shape an irradiation field of a beam with high accuracy, the size of the beam is increased by wobbler electromagnets which deflect the beam trajectory in a circular pattern, so that a uniform irradiation field is shaped by a metal collimator, and the like, so as to correspond to the cross sectional shape of cancer. However, when the metal collimator is adopted, much cost and time are consumed to manufacture the metal collimator. In addition, there is a problem that, when the broadened beam is shaped by the metal collimator, unintended radiation, such as a neutron beam, a gamma ray, and a proton beam, is generated to influence the accuracy of dose estimation.

To cope with this, an invention entitled "Charged Particle Beam Apparatus and Its Operation Method" is proposed in Patent Literature 1. With the invention described in Patent Literature 1, in the state where horizontal irradiation points and a required irradiation dose of a charged particle beam are determined beforehand by a calculation program software 131 on the basis of information on a lesion shape, and the like, and where the interval between the horizontal irradiation points is preferably set to about a half or less of the diameter of the charged particle beam expanded by a scattering body 300, a power supply apparatus 160 of electromagnets 220 and 221 used for setting the irradiation position is modulated by a control apparatus 132 so as to enable a uniform irradiation field to be shaped with a reduced loss of the charged particle beam (2).

Figure 4:
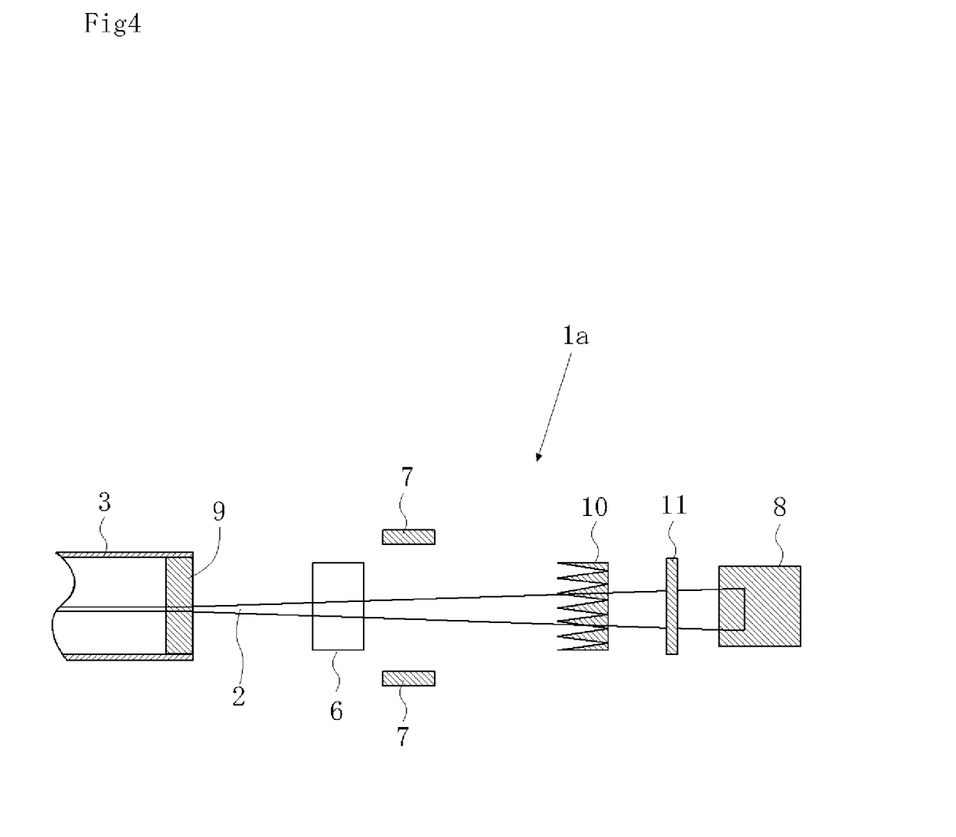
FIG. 4 is a schematic view showing a conventional beam irradiation apparatus.

The principle of the invention is based on the scanning method in which, as in a beam irradiation apparatus 1a shown in FIG. 4, a beam 2, taken out in the atmosphere after passing through a scattering body 9 provided at an end portion of a vacuum transport pipe 3, is modulated and irradiated onto an irradiation target 8 by being scanned transversely (in the horizontal direction (X-axis direction) and the vertical direction (Y-axis direction)) by using XY axis direction scanning electromagnets 6 and 7.

Further, in the invention described in Patent Literature 1, as shown in FIG. 4, a moderator (range shifter 11), which has adjustable thickness and which reduces the beam energy, is provided subsequently to the transverse direction scanning electromagnets 6 and 7, and the reaching distance (range) of the beam in the inside of the body is adjusted by making the beam 2 pass through the range shifter 11. Further, the beam 2 is dispersed by a ridge filter 10 in the traveling direction of the beam, so that a large irradiation field in the irradiation target 8 is obtained. However, the beam 2 is "dispersed" by passing through the range shifter 11, and hence the beam diameter is conventionally limited to about 10 mm according to (2).

Figure 3:
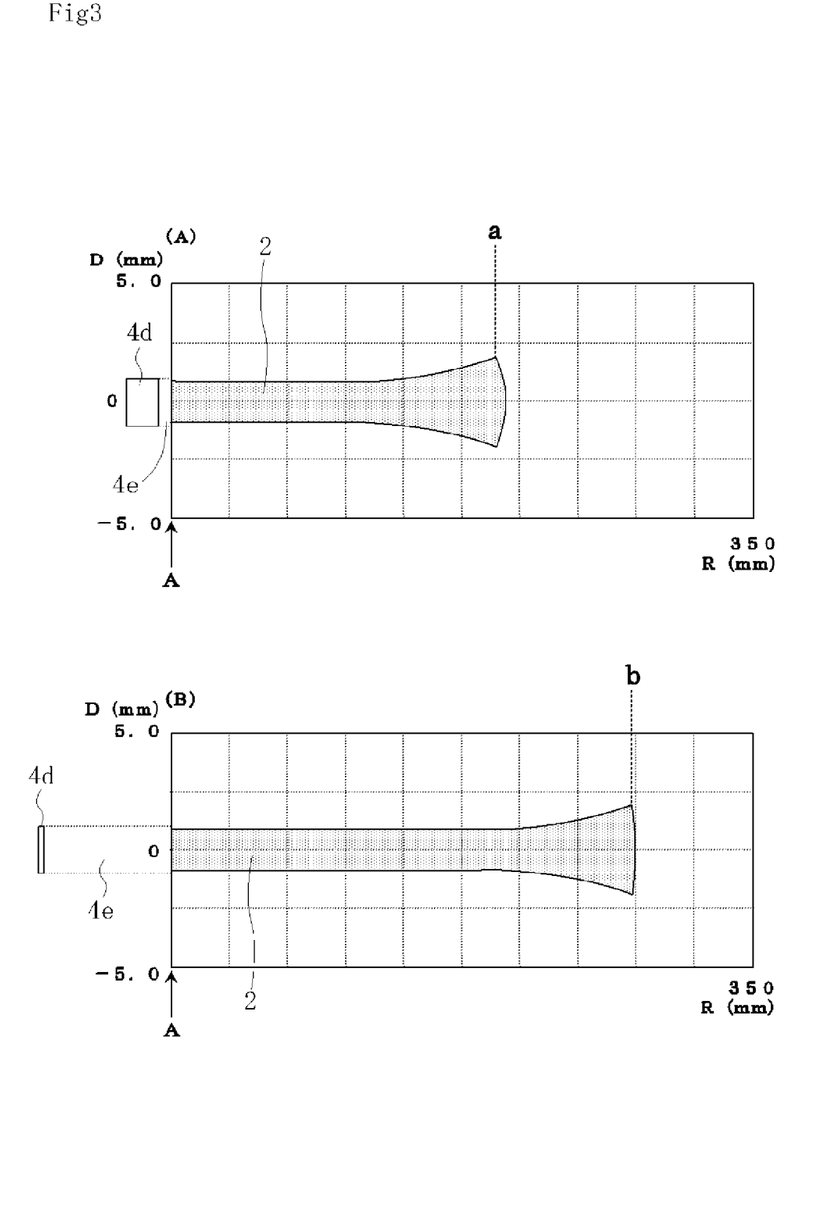
FIG. 3 shows calculation results of beam diameter changes in an irradiation target at the time when the beam range is changed by changing the thickness of the movable range shifter and the distance between the movable range shifter and the irradiation target in the beam irradiation apparatus shown in FIG. 1.
Figure 5:
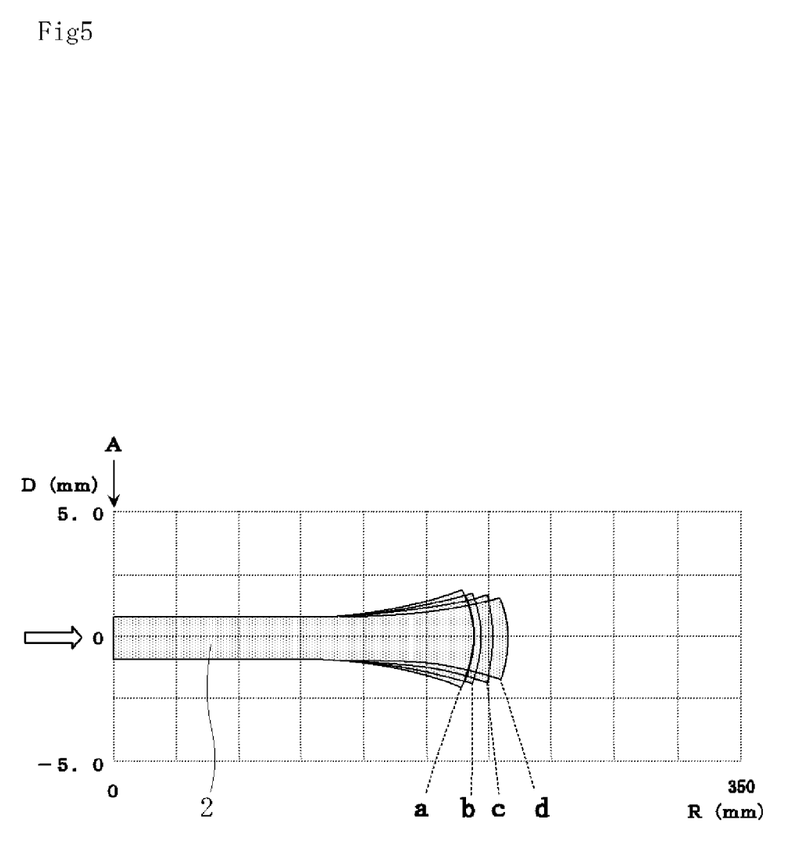
FIG. 5 shows calculation results of beam diameter changes in an irradiation target at the time when the beam range is changed by changing the thickness of the range shifter in the beam irradiation apparatus shown in FIG. 4.

FIG. 5 shows results of calculation of the change in the diameter of the beam in the irradiation target when the beam range is changed by changing the thickness of the range shifter in the beam irradiation apparatus shown in FIG. 4. The calculation was performed by using the beam optics calculation software "WinAgile" under the conditions that the beam energy was set to 235 MeV/u, and that the distance between the scattering body 9 and the body surface was set to 2 mm. FIG. 3 also shows results of calculation performed under the similar conditions.

In FIG. 5, the ordinate (D) represents the beam diameter (mm), and the abscissa (R) represents the beam range (mm). The frame left end indicated by arrow A corresponds to the surface of the irradiation target 8. The ordinate value of 0 corresponds to the design orbit of the beam. In FIG. 5, the beam diameter is set to about 2 mm. The abscissa (R) is set in a range of 350 mm from the abscissa value of 0 (the surface A of the irradiation target).

The calculation result "a" represents a beam behavior at the time when the thickness of the range shifter 11 is set to 30 mm. At this time, the maximum beam diameter at the maximum depth of the beam 2 is 3.828 mm. The calculation result "b" represents a beam behavior at the time when the thickness of the range shifter 11 is set to 20 mm. At this time, the maximum beam diameter at the maximum depth of the beam 2 is 3.666 mm. The calculation result "c" represents a beam behavior at the time when the thickness of the range shifter 11 is set to 10 mm. At this time, the maximum beam diameter at the maximum depth of the beam 2 is 3.3486 mm. The calculation result "d" represents a beam behavior at the time when the thickness of the range shifter 11 is set to 0 mm. At this time, the maximum beam diameter at the maximum depth of the beam 2 is 3.342 mm.

The beam range in the calculation result "a" is different from the beam range in the calculation result "d" by 30 mm, but the difference in the maximum beam diameter between the calculation result "a" and the calculation result "b" at this time is about 0.5 mm.

Further, an invention entitled "Particle Beam Irradiation Apparatus and Particle Beam Therapy Apparatus" described in Patent Literature 2 also discloses a beam irradiation apparatus which modulates the beam diameter. The particle beam irradiation apparatus according to the invention described in Patent Literature 2 is configured by including: a variable range shifter 4 which reduces the energy of a charged particle beam; a quadrupole magnet 6 which converges the divergence of the charged particle beam due to the scattering in the variable range shifter 4 by modulating the excitation amplitude of the electromagnet in correspondence with the energy of the charged particle beam reduced in the variable range shifter 4; and a scanning magnet 8 which changes the beam trajectory of the charged particle beam, and is configured such that an increase in the beam diameter of the charged particle beam due to the scattering in the range shifter can be reduced so that a charged particle beam having a small beam diameter can be supplied to enable spatially accurate irradiation to be performed to a body to be irradiated, and such that the range shifter can be arranged at a position separated from a patient, so as to eliminate an intimidating feeling due to the mechanical noize, and the like, of the range shifter.

In Patent Literature 2, the quadrupole magnet 6 is adopted to modulate, in the non-vacuum environment, the trajectory of the beam emitted from the transport pipe. However, since the quadrupole magnet 6 is arranged on the downstream side of the variable range shifter 4, the betatron function of the beam is destroyed at the time when the beam passes through the variable range shifter 4, and the emittance of the beam is increased. Therefore, in order to actually focus the beam, a distance of about 10 m needs to be provided between the variable range shifter 4 and the quadrupole magnet 6. The straight portion of the extraction port including the transport pipe and the extraction nozzle generally has a length of 10 m or less, and hence, even when the quadrupole magnet 6 is arranged on the downstream side of the variable range shifter 4, it is very difficult to plan the arrangement in which the diameter of the beam is maintained to be small until the beam reaches the inside of the irradiation target. Further, the beam diameter is changed by about 0.5 mm due to the thickness of the variable range shifter 4 as described above, and hence, in order to adjust the change in the beam diameter, it is necessary to highly accurately adjust the excitation pattern of the quadrupole magnet 6 for each of the variable range shifter 6 having different thicknesses. However, for the practical use of the technique disclosed in Patent Literature 2, a large amount of labor is required because it is necessary to manage the accuracy of the power supply of the quadrupole magnet 6 and to cope with the increase in the number of excitation patterns of the quadrupole magnet 6. Therefore, with the technique disclosed in Patent Literature 2, it is actually difficult to shape a beam having a diameter of several millimeters or less.

Until now, no technique has been known for shaping, in a target, a therapeutic beam having a diameter of about several millimeters or less without using a collimator. Further, no method has also been known for modulating the beam spot size in the irradiation target 8 with high accuracy of, for example, 0.1 mm or less, while securing a wide irradiation field.

CITATION LIST

Patent Literature

Patent Literature 1: Japanese Patent Laid-Open No. 10-118204
Patent Literature 2: Japanese Patent Laid-Open No. 2009-22797

SUMMARY OF INVENTION

Technical Problem

Accordingly, an object of the present invention is to provide a beam irradiation apparatus which can shape a beam having a diameter much smaller than the conventional beam diameter, and which can highly accurately modulate the beam diameter, the beam range, and the beam trajectory, and is also to provide a beam irradiation control method which can highly accurately modulate the range of the irradiation field in an irradiation target.

Solution to Problem

In order to solve the above-described problems, according to the present invention, there is provided a beam irradiation apparatus featured by including a transport pipe which is vacuum-evacuated to be used as a transport channel of a beam taken out from an accelerator, and a quadrupole magnet which modulates the diameter of the beam so that the beam is incident on an irradiation target existing in the atmosphere while maintaining the focusing angle of the beam. Further, the beam irradiation apparatus according to the present invention is featured by including one or more longitudinally movable range shifters which are provided to be able to change the distance to the irradiation target of the beam and which modulate the beam range by reducing energy of the beam by allowing the beam to pass through the movable range shifter, and is featured in that the beam is irradiated onto the irradiation target by modulating a beam range by using, as a second range shifter, a non-vacuum space between the movable range shifter and the irradiation target. Further, the beam irradiation apparatus according to the present invention is featured in that the movable range shifter is located at a distal end of a vacuum-evacuated extraction nozzle which is connected, via a vacuum diaphragm, to an end portion of the transport pipe in an expandable and contractible manner. Further, any of the above-described beam irradiation apparatuses according to the present invention is featured in that each of the movable range shifters can be inserted and retracted with respect to the beam axis to enable the thickness of the movable range shifter to be changed. Further, any of the above-described beam irradiation apparatuses according to the present invention is featured by including, on an outer periphery of the transport pipe and on a downstream side of the quadrupole magnet, a pair of X-axis direction scanning electromagnets arranged to face each other, and a pair of Y-axis direction scanning electromagnets arranged to face each other, and is featured in that a trajectory of the beam is modulated by using the X-axis direction scanning electromagnets and the Y-axis direction scanning electromagnets.

In addition, a method for controlling beam irradiation according to the present invention is featured in that a beam taken out from an accelerator into a high vacuum transport pipe is strongly focused in the transport pipe by using a quadrupole magnet, to modulate the diameter of the beam, and then the strongly focused beam is injected onto an irradiation target. Further, the method for controlling beam irradiation according to the present invention is featured in that the beam is irradiated onto the irradiation target by modulating a beam range by making the beam pass through one or more longitudinally movable range shifters which are continuously connected to the transport pipe via a vacuum diaphragm and which are provided to enable a distance to the irradiation target of the beam to be changed to modulate the beam range by reducing the energy of the beam, and by making the beam further pass through a non-vacuum space between the movable range shifter and the irradiation target, the distance of which space can be changed. Further, the method for controlling beam irradiation according to the present invention is featured in that the beam diameter and the beam range are modulated by changing the distance of the space in a range of 0 to 100 cm. Further, any of the above described methods for controlling beam irradiation according to the present invention is featured in that the strong focusing enables the beam to maintain the focusing angle of the beam until the beam reaches the aimed depth in the irradiation target.

Further, a heavy particle radiotherapy apparatus for medical purposes according to the present invention is featured by including: a transport pipe which is vacuum-evacuated to be used as a transport channel of a beam taken out from an accelerator; a quadrupole magnet which modulates a diameter of the beam so that the beam is incident on an irradiation target existing in the atmosphere while maintaining a focusing angle of the beam; one or more longitudinally movable range shifters which are provided at a distal end of a vacuum-evacuated extraction nozzle connected, via a vacuum diaphragm, to an end portion of the transport pipe in an expandable and contractible manner, to enable a distance to the irradiation target of the beam to be changed, and which modulate a beam range by reducing energy of the beam by allowing the beam to pass through the movable range shifter, a thickness of which can be changed by enabling each of the movable range shifters to be inserted and retracted with respect to a beam axis; and a pair of X-axis direction scanning electromagnets and a pair of Y-axis direction scanning electromagnets, each pair of the pairs of scanning electromagnets being arranged on an outer periphery of the transport pipe and on a downstream side of the quadrupole magnet to face each other, and is featured in that the beam is irradiated onto the irradiation target by modulating the beam diameter, a beam trajectory, and the beam range by using, as a second range shifter, a non-vacuum space between the movable range shifter and the irradiation target.

Advantageous Effects of Invention

The present invention exhibits following effects by the configurations as described above. In the present invention, the quadrupole magnet is adopted which strongly focuses the beam in the transport pipe on the upstream side of the movable range shifter so as to enable the focusing angle of the beam to be maintained even in the vicinity of the irradiation target, and hence the beam can be shaped to have a very small diameter of several millimeters or less in the irradiation target.

Further, in the present invention, the irradiation control of the beam having the beam diameter of several millimeters or less can be highly accurately performed in about 0.1 mm increments and further 0.01 mm increments. Therefore, when the irradiation target is a human body, the beam can be irradiated onto a lesion more accurately and effectively as compared with the conventional beam irradiation therapy, and hence damage (exposure) of normal portions and a burden to the patient are reduced. When the present invention is applied to beam irradiation therapy, the beam irradiation therapy can be used for many diseases and can used in a wide application range at low cost. For example, the present invention is suitable for beam irradiation therapy of diseases, such as pituitary tumor, intravascular tumor, and age-related macular degeneration, which are difficult to be treated.

Further, in the present invention, objects, for example, an irradiation field shaping instrument, such as a metal collimator, and a ridge filter, which are installed on the beam line in order to shape an irradiation shape, are not indispensable. Therefore, it is possible to reduce the error in dose estimation due to the generation of neutrons and scattering particles which are generated at the time when the beam collides with the objects, and hence it is possible to estimate the irradiation dose with high accuracy.

Further, in the present invention, a quadrupole magnet is not needed in the very vicinity of the irradiation target for final focusing of the beam, and hence it is possible to secure the irradiation field as widely as in the case of irradiation by the conventional dispersed beam. Further, when the quadrupole magnet is not excited, the beam irradiation apparatus according to the present invention can also be operated to perform the above described conventional beam irradiation methods (1) and (2).

In addition, the present invention can be applied regardless of the types of cyclotron and synchrotron accelerators, and regardless of particle ion species, such as protons and heavy particles, and hence the present invention has high versatility.

DESCRIPTION OF EMBODIMENT

In the following, a beam irradiation apparatus and a beam irradiation control method according to the present invention will be described.

Embodiment 1

Figure 1:
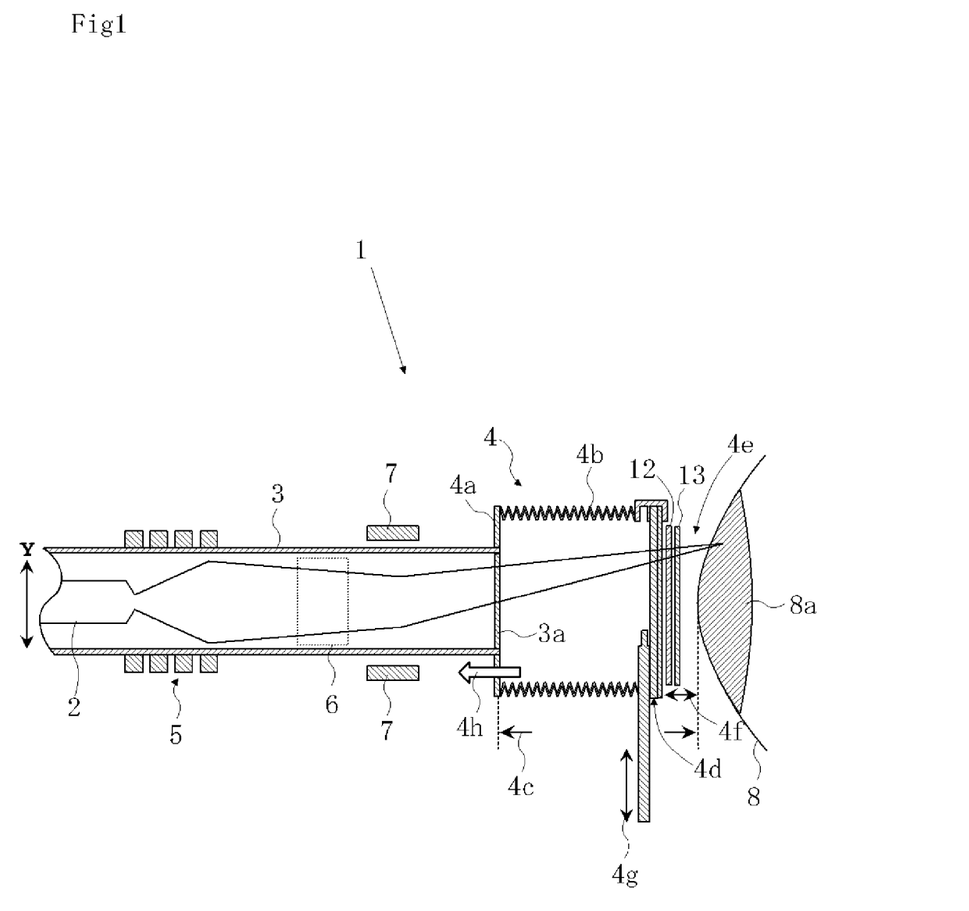
FIG. 1 is a schematic view showing a beam irradiation apparatus according to the present invention.

As shown in FIG. 1, a beam irradiation apparatus 1, which is one example according to the present invention, is configured by a transport pipe 3, an extraction nozzle 4 provided with a longitudinally movable range shifter 4*d*, a quadrupole magnet 5, and XY axis direction scanning electromagnets 6 and 7.

The transport pipe 3, which is the same as conventional one, is a hollow pipe which is connected to an accelerator and is highly evacuated, and through which a beam taken out from the accelerator passes toward an irradiation target.

The extraction nozzle 4 is configured by an extension section 4a which is extended to be continuously connected to the transport pipe 3 via a vacuum diaphragm 3a, an expanding/contracting section 4b which is connected to the extension section 4a so as to be expandable and contractible, and the movable range shifter 4d which is provided at the end portion of the expanding/contracting section 4b on the side opposite to the side of the transport pipe 3 so as to be slidable in the sliding direction 4g. The extraction nozzle 4 is continuously connected to the transport pipe 3 in a vacuum state as it is. The expanding/contracting section 4b has so-called a bellows shape, and is made of a metal material, such as stainless steel, so as to withstand evacuation 4h. The vacuum diaphragm 3a enables the degree of vacuum in the transport pipe 3 and the degree of vacuum in the extraction nozzle 4 to be set independently of each other.

However, the degree of vacuum in the extraction nozzle 4 does not need to be as high as the degree of vacuum (about $10^{-7}$ Pa) of the chamber in the synchrotron, and the extraction nozzle 4 sufficiently exhibits its function when the degree of vacuum in the extraction nozzle 4 is set as low as about 1 Pa or less, at which degree the air as scattering material can be neglected.

A space 4e between the movable range shifter 4d and an irradiation target 8 is usually maintained in the atmosphere in which oxygen, nitrogen, other gases, and water vapor exist in a mixed state. Therefore, when the beam 2 passes through the space 4e, the energy of the beam 2 is reduced. That is, the space 4e functions as a second range shifter. For this reason, the beam range can be modulated by changing the distance 4f of the space 4e between the distal end of the movable range shifter 4d and the irradiation target 8 by expanding and contracting the expanding/contracting section 4b.

The movable range shifter 4d modulates the beam range in the irradiation target 8 by reducing the beam energy. The movable range shifter 4d is made of a material similar to a conventionally used material, and is made of a plurality of plastic plates, such as acrylic plates, which have different thicknesses as required.

Note that the position at which the movable range shifter 4d is moved is not limited to the position shown in FIG. 1, and the movable range shifter 4d may also be provided so as to be movable in the end portion of the transport pipe 3. The method for moving the movable range shifter 4d is not limited in particular, as long as the width 4c of movement of the irradiation point can be changed by a signal from the outside, and as long as the irradiation point can be fixed at an arbitrary position.

It is preferred that the distance 4f between the movable range shifter 4d and the irradiation target 8 is set to about 0 cm to about 100 cm. The space 4e between the movable range shifter 4d and the irradiation target 8 is usually an air layer, and hence the beam 2 is diffused in the space 4e. In almost all beam irradiation, the beam is focused on a point in front of the irradiation target. The diameter of the beam 2 is enlarged at a divergence angle after the beam 2 passes through the focal point. When the distance 4f of the space 4e is set to 100 cm or more, and when the beam 2 is made incident on an irradiation field 8a at the divergence angle, the diameter of the beam 2 cannot be reduced to a small value, and also the diameter of the beam 2 cannot be accurately modulated. Therefore, it is necessary that the transport pipe 3 is installed to be in contact with the irradiation target 8 or extended to the vicinity of the irradiation target 8.

The quadrupole magnet 5 is a beam convergence electromagnet which has been conventionally used in the accelerator and which is arranged on the outer periphery of the transport pipe 3 to strongly focus the beam 2 in the transport pipe 3 arranged on the upstream side of the movable range shifter 4d. It is necessary that the beam 2 is strongly focused so as to maintain the focusing angle even after the beam 2 passes through the movable range shifter 4d, the space 4e, and the irradiation target 8. The modulation of the convergence width of the beam 2 is performed in such a manner that the beam 2 is transported in the transport pipe 3 so that the diameter of the beam is sufficiently increased by the quadrupole magnet 5, and that the quadrupole magnet 5 is excited so as to focus the beam 2 simultaneously in the X-axis and Y-axis directions. When the focusing width of the beam 2 is modulated in this way, the beam 2 can be made to reach the inside of the irradiation target in the state where the focusing angle of the beam is maintained.

The X-axis direction scanning electromagnet 6 is a pair of electromagnets which are arranged on the outer periphery of the transport pipe 3 and between the quadrupole magnet 5 and the movable range shifter 4d so as to face each other, and modulates the beam trajectory in the X-axis direction in such a manner that a deflecting force applied to the beam 2 according to the Fleming's law is changed over time by changing the current flowing through the pair of electromagnets.

The Y-axis direction scanning electromagnet 7 is a pair of electromagnets which are arranged on the outer periphery of the transport pipe 3 and between the quadrupole magnet 5 and the movable range shifter 4d so as to face each other, and modulates the beam trajectory in the Y-axis direction similarly to the X-axis direction scanning electromagnet 6.

Further, the beam irradiation apparatus 1, which includes the XY axis direction scanning electromagnets 6 and 7, and in which the extraction nozzle 4 is extended, is hence capable of securing a wide irradiation field 8a having the diameter or more of the transport pipe 3. Further, when the quadrupole magnet 5 is not excited, a diffused beam having a diameter similar to that of the conventional beam irradiation apparatus can also be irradiated.

Further, the beam irradiation apparatus 1 includes, in the space 4e, a dose monitor 12 and a position monitor 13 of the beam, which are conventionally used. Note that the dose monitor 12 and the position monitor 13 may be installed in the vicinity of (in a range of several millimeters or less) the movable range shifter in the extraction nozzle 4. In this case, it is necessary that the dose monitor 12 and the position monitor 13 can be retracted from the beam trajectory at the time when the beam is irradiated onto the irradiation target 8.

Beam irradiation data can be acquired by the various monitors, and the acquired data can also be used as adjustment data for the next irradiation. Further, the beam irradiation apparatus 1 may include a ridge filter 10 as required. The ridge filter, which is similar to that conventionally used, diffuses the beam in the traveling direction of the beam and expands the irradiation field in the beam traveling direction.

The beam irradiation apparatus 1, configured as described above, can modulate the beam trajectory and the irradiation dose on the basis of the signals, and the like, from the respective monitors similarly to the conventional manner, and further can modulate the beam diameter, the beam range, and the beam trajectory with high accuracy by changing the thickness of the movable range shifter 4d and the distance 4f of the space 4e. FIG. 1 shows a trajectory of the beam 2, which is deflected in the Y-axis direction (indicated by double-headed arrow Y in FIG. 1) by the Y-axis direction scanning electromagnet 7.

Figure 2:
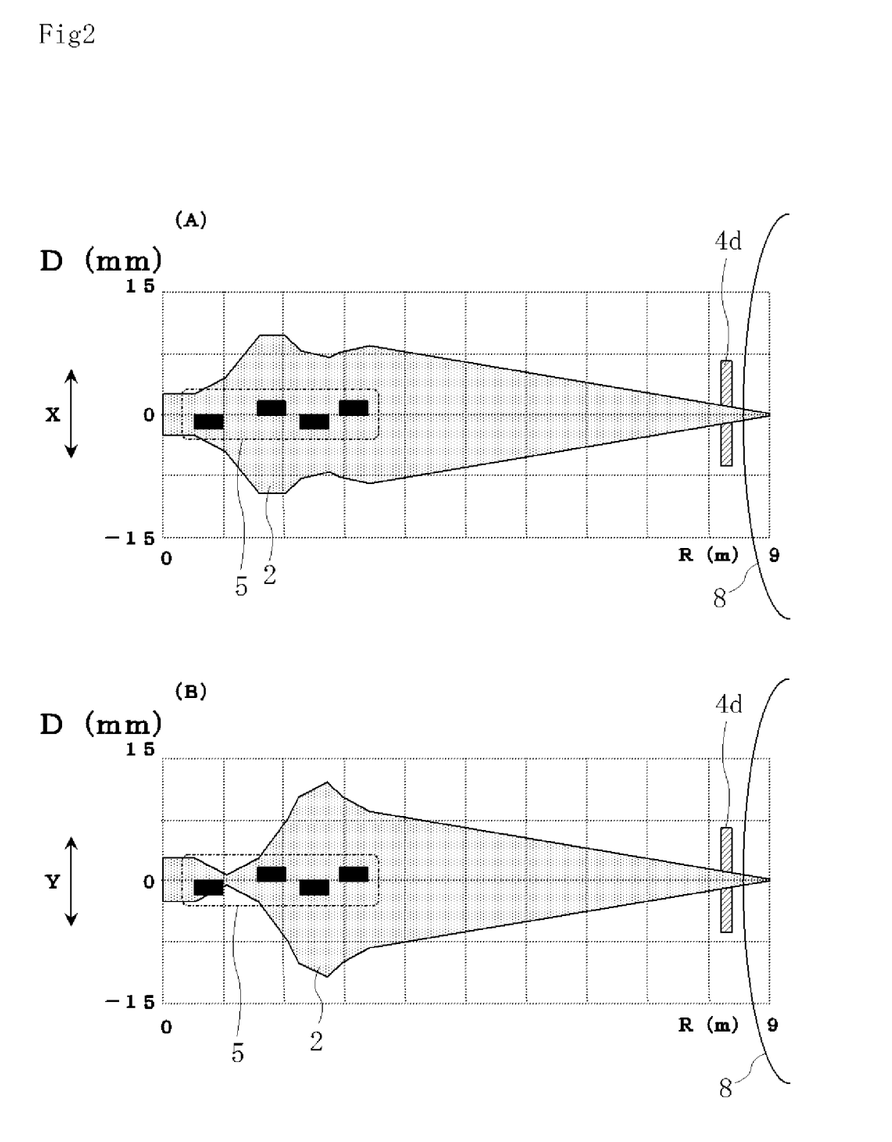
FIG. 2 shows calculation results of beam diameter changes caused at the time when a beam is transported in the beam irradiation apparatus according to the present invention.

FIG. 2 shows calculation results of beam diameter changes caused at the time when a beam is transported in the beam irradiation apparatus 1 configured as shown in FIG. 1. FIG. 2(A) is a cross-sectional view showing a beam diameter in the X-axis (horizontal) direction (indicated by double-headed arrow X in FIG. 2), and FIG. 2(B) is a cross-sectional view showing a beam diameter in the Y-axis (vertical) direction (indicated by double-headed arrow Y in FIG. 2) perpendicular to the X-axis. In both FIG. 2(A) and FIG. 2(B), the ordinate represents the beam diameter (mm), and the abscissa represents the length of the beam transport system (m), whose length is set to 9 m in this case.

As can be seen from FIG. 2(A) and FIG. 2(B), in the beam irradiation apparatus 1 configured as described above, the beam 2 is strongly focused by the quadrupole magnet 5 and focused toward the irradiation target 8. Further, the focusing angle of the beam 2 can be maintained until the beam 2 reaches the irradiation position in the irradiation target 8. Therefore, when the beam is irradiated by the beam irradiation apparatus 1 according to the present invention, the beam can be made to reach the irradiation field of the irradiation target 8 while the very small diameter of the beam is maintained as it is.

The focusing angle of the beam is made to be maintained in order that the beam diameter of 2 to 3 mm is maintained even in the irradiation target 8. By the strong focusing in the beam irradiation apparatus according to the present invention, a very small beam diameter, which cannot be obtained in the conventional beam irradiation apparatus, can be obtained in the state where conditions enabling the scanning of a large irradiation field are satisfied.

In the case of using a beam extraction method in which a beam is not taken out at a focusing angle, a beam having a diameter of 2 to 3 mm cannot be formed without using a collimator having a metal slit. Further, when the metal slit is used, a large irradiation field cannot be secured. There has been a design which satisfies one of the requirements of a large irradiation field, a small beam diameter, and a function of irradiation adjustment in 0.1 mm increments. However, the design, which simultaneously satisfies all the requirements, can be realized for the first time in the beam irradiation apparatus according to the present invention. With present invention, it is possible to realize a beam irradiation apparatus, which can be used as a high-accuracy particle beam therapy port and also used as a general purpose irradiation port without changing the layout of the apparatus. Further, with the present invention, both highly accurate use of the beam and highly efficient operation of the treatment room, which are conventionally in the relationship of antinomy each other, can be realized at a high level for the first time.

FIG. 3 shows calculation results of beam diameter changes in an irradiation target at the time when the beam range is changed by changing the thickness of the movable range shifter and the distance between the movable range shifter and the irradiation target in the beam irradiation apparatus shown in FIG. 1.

In both FIG. 3(A) and FIG. 3(B), the abscissa (R) represents the beam reaching distance (R: mm) from the body surface A, whose distance is set to 350 mm here. The ordinate (D) represents the beam diameter (mm). The left end of the frame, which is represented by arrow A, corresponds to the surface of the irradiation target 8. The ordinate value of 0 corresponds to the center of the beam. In FIG. 3, the diameter of the initial beam is set to about 2 mm. Note that the broken-dotted lines in FIG. 3(A) and FIG. 3(B) respectively show calculation results in the case where a beam having a beam diameter of 2 mm is made incident on the irradiation target 8 at a conventional divergence angle without the beam being strongly focused in the transport pipe 3.

The broken line "a" in FIG. 3 shows the behavior of the beam in the case where the thickness of the movable range shifter 4d is set to 30 mm and where the space 4e is set to 20 mm. In this case, the maximum beam diameter at the maximum depth of the beam 2 is 3.828 mm. The broken line "b" in FIG. 3 shows the behavior of the beam in the case where the thickness of the movable range shifter 4d is set to 2 mm and where the space 4e is set to 150 mm. In this case, the maximum beam diameter at the maximum depth of the beam 2 is 3.918 mm.

As shown in FIG. 3, with the beam irradiation apparatus 1 according to the present invention, even when the beam range is changed by changing the thickness of the movable range shifter 4d and the distance 4f of the space 4e, the maximum beam diameter at the maximum depth of the beam is changed only by about 0.1 mm, which is very small. On the other hand, when a conventional beam is made incident on the irradiation target 8 at a divergence angle, although the beam diameter at the time of incidence is set to be the same as the beam diameter shown by broken lines in FIG. 3, the beam diameter at the maximum depth of the beam is increased about five times as large as the beam diameter at the time of incidence. That is, with the conventional method, even when the beam diameter is reduced beforehand by using an instrument, such as a collimator, to any degree, the diameter of the beam is increased in the vicinity of the maximum depth of the beam due to the scattering of the beam itself. Further, as shown in FIG. 3(A) and FIG. 3(B), in the case of the conventional beam which is not strongly focused in the transport pipe 3, the beam range cannot be changed even by changing the distance of the space 4e. Therefore, when the beam 2 is strongly focused by the quadrupole magnet, and when the range of the beam 2 is modulated by changing the thickness of the movable range shifter 4d and by using, as the second range shifter, the space 4e having a variable distance, the beam 2 can be irradiated onto the irradiation target 8 by modulating the beam range while highly accurately modulating the beam diameter in 0.1 mm increments.

Further, when the thickness of the movable range shifter 4d and the distance 4f of the space 4e are more accurately modulated, the beam diameter can be modulated sufficiently even in about 0.01 mm increments. As can be seen by comparing the relationship between the change in the beam range and the beam diameter shown in FIG. 3 with the relationship between the change in the beam range and the beam diameter shown in FIG. 5, the present invention enables the beam diameter to be modulated with a degree of accuracy which cannot be conventionally achieved.

Industrial Applicability

With the beam irradiation apparatus and the beam irradiation method according to the present invention, in which the beam diameter of a beam taken out from an accelerator can be reduced to a very small value which cannot be conventionally achieved, and in which the beam diameter, the beam range, and the beam trajectory can be modulated with high accuracy, it is possible to modulate the beam irradiation position and the beam irradiation field with high accuracy. Therefore, the present invention can be applied to all industrial fields using the beam irradiation, and is particularly effective for a beam irradiation apparatus, for example, a particle beam therapy apparatus. Therefore, the introduction of the present invention is expected.

REFERENCE SIGNS LIST

1 Beam irradiation apparatus
1a Beam irradiation apparatus
2 Beam
3 Transport pipe
3a Vacuum diaphragm
4 Extraction nozzle
4a Extension section
4b Expanding/contracting section
4c Moving width
4d Movable range shifter
4e Space
4f Distance
4g Sliding direction
4h Exhaust
5 Quadrupole magnet
6 X-axis direction scanning electromagnet
7 Y-axis direction scanning electromagnet
8 Irradiation target
9 Scattering body
10 Ridge filter
11 Range shifter
12 Dose monitor
13 Position monitor

The invention claimed is:

1. A beam irradiation apparatus comprising:
 a vacuum-evacuated transport pipe for transporting a beam from an accelerator;
 a quadrupole magnet on an outer periphery of the vacuum-evacuated transport pipe, and which is configured to control a diameter of the beam by strongly focusing the beam so that the beam is incident on an irradiation target existing in the atmosphere while maintaining a focusing angle of the beam; and
 a vacuum-evacuated extraction nozzle which is connected, via a vacuum diaphragm, to an end portion of the vacuum-evacuated transport pipe,
 wherein the vacuum-evacuated extraction nozzle comprises an expanding-contracting section which retractably extends from the end portion of the vacuum-evacuated transport pipe.

2. The beam irradiation apparatus according to claim 1, further comprising one or more longitudinally movable range shifters which are configured to modulate a beam range by reducing energy of the beam by allowing the beam to pass through the one or more longitudinally movable range shifters, and
 wherein the expanding-contracting section of the vacuum-evacuated extraction nozzle is configured to modulate the beam range by changing a distance of a non-vacuum space between the one or more longitudinally movable range shifters and the irradiation target.

3. The beam irradiation apparatus according to claim 2, wherein the vacuum-evacuated extraction nozzle further comprises an extension section which is continuously connected to the vacuum-evacuated transport pipe and which extends perpendicularly from the vacuum-evacuated transport pipe.

4. The beam irradiation apparatus according to claim 2, wherein each of the one or more longitudinally movable range shifters is adapted to be slidably inserted into the vacuum-evacuated extraction nozzle with respect to a beam axis, to change a combined thickness of the one or more longitudinally movable range shifters.

5. The beam irradiation apparatus according to claim 4, further comprising, on the outer periphery of the vacuum-evacuated transport pipe and on a downstream side of the quadrupole magnet, a pair of X-axis direction scanning electromagnets arranged to face each other, and a pair of Y-axis direction scanning electromagnets arranged to face each other,
 wherein the pair of X-axis direction scanning electromagnets and the pair of Y-axis direction scanning electromagnets are configured to modulate a trajectory of the beam.

6. The beam irradiation apparatus according to claim 2, further comprising, on the outer periphery of the vacuum-evacuated transport pipe and on a downstream side of the quadrupole magnet, a pair of X-axis direction scanning electromagnets arranged to face each other, and a pair of Y-axis direction scanning electromagnets arranged to face each other,
 wherein the pair of X-axis direction scanning electromagnets and the pair of Y-axis direction scanning electromagnets are configured to modulate a trajectory of the beam.

7. The beam irradiation apparatus according to claim 1, wherein the vacuum-evacuated extraction nozzle further comprises an extension section which is continuously connected to the vacuum-evacuated transport pipe and which extends perpendicularly from the vacuum-evacuated transport pipe.

8. The beam irradiation apparatus according to claim 7, wherein each of the one or more longitudinally movable range shifters is adapted to be slidably inserted into the vacuum-evacuated extraction nozzle with respect to a beam axis, to change a combined thickness of the one or more longitudinally movable range shifters.

9. The beam irradiation apparatus according to claim 7, further comprising, on the outer periphery of the vacuum-evacuated transport pipe and on a downstream side of the quadrupole magnet, a pair of X-axis direction scanning electromagnets arranged to face each other, and a pair of Y-axis direction scanning electromagnets arranged to face each other,
 wherein the pair of X-axis direction scanning electromagnets and the pair of Y-axis direction scanning electromagnets are configured to modulate a trajectory of the beam.

10. The beam irradiation apparatus according to claim 1, further comprising, on the outer periphery of the vacuum-evacuated transport pipe and on a downstream side of the quadrupole magnet, a pair of X-axis direction scanning electromagnets arranged to face each other, and a pair of Y-axis direction scanning electromagnets arranged to face each other,
 wherein the pair of X-axis direction scanning electromagnets and the pair of Y-axis direction scanning electromagnets are configured to modulate a trajectory of the beam.

11. A beam irradiation control method, comprising:
 strongly focusing a beam in a vacuum-evacuated transport pipe using a quadrupole magnet, the beam having been emitted from an accelerator,
 modulating a diameter of the beam in increments of 0.1 mm or less, and
 irradiating the beam onto an irradiation target,
 wherein strongly focusing the beam in the vacuum-evacuated transport pipe maintains a focusing angle of the beam until the beam reaches the irradiation target.

12. The beam irradiation control method according to claim 11, further comprising:

controlling a beam range by passing the beam through one or more longitudinally movable range shifters, and optionally passing the beam through a distance of a non-vacuum space between the one or more longitudinally movable range shifters and the irradiation target, wherein each of the one or more longitudinally movable range shifters is adapted to be slidably inserted into a vacuum-evacuated extraction nozzle which is connected, via a vacuum diaphragm, to the vacuum-evacuated transport pipe, wherein the one or more longitudinally movable range shifters are configured to modulate a beam range by reducing energy of the beam by allowing the beam to pass through the one or more longitudinally movable range shifters, and wherein the distance of the non-vacuum space between the one or more longitudinally movable range shifters and the irradiation target can be changed.

13. The beam irradiation control method according to claim 12, wherein the distance of the non-vacuum space between the one or more longitudinally movable range shifters and the irradiation target is in a range of 0 to 100 cm.

14. A heavy particle radiotherapy apparatus for medical purposes, comprising:

a vacuum-evacuated transport pipe for transporting a beam from an accelerator;

a quadrupole magnet on an outer periphery of the vacuum-evacuated transport pipe and which is configured to modulate a diameter of the beam by strongly focusing the beam so that the beam is incident on an irradiation target existing in the atmosphere while maintaining a focusing angle of the beam;

a vacuum-evacuated extraction nozzle which is connected, via a vacuum diaphragm, to an end portion of the vacuum-evacuated transport pipe and which comprises an expanding-contracting section that retractably extends from the end portion of the vacuum-evacuated transport pipe;

one or more longitudinally movable range shifters which are provided at a distal end of the vacuum-evacuated extraction nozzle, each of the one or more longitudinally movable range shifters being adapted to be slidably inserted into the vacuum-evacuated extraction nozzle with respect to a beam axis, to change a combined thickness of the one or more longitudinally movable range shifters; and a pair of X-axis direction scanning electromagnets that face each other and a pair of Y-axis direction scanning electromagnets that face each other, each of the pair of X-axis direction scanning electromagnets and the pair of Y-axis direction scanning electromagnets being arranged on the outer periphery of the vacuum-evacuated transport pipe and on a downstream side of the quadrupole magnet, wherein the one or more longitudinally movable range shifters are configured to modulate a beam range by reducing the energy of the beam by allowing the beam to pass through the one or more longitudinally movable range shifters, and wherein the expanding-contracting section of the vacuum-evacuated extraction nozzle is configured to modulate the beam range by changing a distance of a non-vacuum space between the one or more longitudinally movable range shifters and the irradiation target.

* * * * *

UNITED STATES PATENT AND TRADEMARK OFFICE
CERTIFICATE OF CORRECTION

PATENT NO. : 8,716,679 B2 Page 1 of 1
APPLICATION NO. : 13/519811
DATED : May 6, 2014
INVENTOR(S) : Torikai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 9 days.

Signed and Sealed this

Twenty-ninth Day of September, 2015

Michelle K. Lee
*Director of the United States Patent and Trademark Office*